United States Patent
Morioka et al.

(10) Patent No.: US 9,714,924 B2
(45) Date of Patent: Jul. 25, 2017

(54) ULTRASONIC INSPECTION DEVICE AND METHOD OF ULTRASONIC INSPECTION

(71) Applicant: Kabushiki Kaisha Toshiba, Minato-ku (JP)

(72) Inventors: Tomoko Morioka, Kanagawa-ken (JP); Naotada Okada, Kanagawa-ken (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 772 days.

(21) Appl. No.: 14/027,397

(22) Filed: Sep. 16, 2013

(65) Prior Publication Data
US 2014/0283610 A1 Sep. 25, 2014

(30) Foreign Application Priority Data

Mar. 22, 2013 (JP) ................................. 2013-061142

(51) Int. Cl.
*G01N 29/04* (2006.01)
*G01N 29/12* (2006.01)
(Continued)

(52) U.S. Cl.
CPC .......... *G01N 29/12* (2013.01); *G01N 29/2418* (2013.01); *G01N 29/46* (2013.01); *G01N 2291/267* (2013.01)

(58) Field of Classification Search
CPC ........... G01N 29/221; G01N 2291/267; G01N 2291/2675; G01N 2291/2677
(Continued)

(56) References Cited

U.S. PATENT DOCUMENTS 5,063,779 A * 11/1991 Landry ................. G01N 29/11
376/252
5,920,014 A * 7/1999 Waschkies ........... B23K 11/252
73/597

(Continued)

FOREIGN PATENT DOCUMENTS

CN    101002670 A    7/2007
CN    101849182 A    9/2010
(Continued)

OTHER PUBLICATIONS

Office Action issued Oct. 15, 2015 in Korean Patent Application No. 10-2014-0024271 (with English language translation).
(Continued)

*Primary Examiner* — Michael A Lyons
*Assistant Examiner* — Suman K Nath
(74) *Attorney, Agent, or Firm* — Oblon, McClelland, Maier & Neustadt, L.L.P.

(57) ABSTRACT

An ultrasonic inspection device includes: a vibration generating section that irradiates laser beam onto a first member to generate ultrasonic vibration; a detecting section that detects the ultrasonic vibration propagated from the first to a second members via a welded portion; and an analyzing section that analyzes the propagated ultrasonic vibration detected by the detecting section. The analyzing section obtains at least one of frequency and wavelength of the ultrasonic vibration detected by the detecting section upon when a displacement in the second member in a thickness direction becomes maximum. The analyzing section obtains a cross sectional dimension of the welded portion from a correlated relationship of the cross sectional dimension of the welded portion obtained in advance at a position on a surface of the second member on the first member side and
(Continued)

the at least one of the frequency and wavelength of the ultrasonic vibration.

20 Claims, 2 Drawing Sheets

(51) Int. Cl.
    *G01N 29/24*     (2006.01)
    *G01N 29/46*     (2006.01)

(58) Field of Classification Search
    USPC .............. 73/643, 622, 624, 648, 598, 588; 356/511
    See application file for complete search history.

(56) References Cited

U.S. PATENT DOCUMENTS

| | | | | |
|---|---|---|---|---|
| 9,052,273 | B2* | 6/2015 | Michaut | B23K 31/125 |
| 2002/0144984 | A1* | 10/2002 | Mori | B23K 26/03 219/121.64 |
| 2011/0286005 | A1* | 11/2011 | Yamamoto | B23K 31/125 356/511 |

FOREIGN PATENT DOCUMENTS

| | | |
|---|---|---|
| CN | 102773607 A | 11/2012 |
| JP | 4-147053 | 5/1992 |
| JP | 4-366761 | 12/1992 |
| JP | 2002-207028 A | 7/2002 |
| JP | 2006-300634 A | 11/2006 |
| JP | 2011-58937 | 3/2011 |
| JP | 102323216 A | 1/2012 |
| JP | 2013-61142 | 4/2013 |
| KR | 10-2010-0012759 A | 2/2010 |

OTHER PUBLICATIONS

Office Action issued Mar. 2, 2016 in Korean Patent Application No. 10-2014-0024271 (with English language translation).
Combined Chinese Office Action and Search Report issued Dec. 24, 2015 in Patent Application No. 201410084662.1 (with English language translation).
Office Action issued Jun. 28, 2016 in Korean Patent Application No. 10-2014-0024271 (with English translation).
Combined Chinese Office Action and Search Report issued Sep. 8, 2016 in Patent Application No. 201410084662.1 (with English language translation).

* cited by examiner

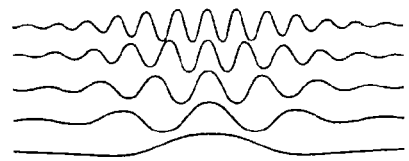
FIG. 2A
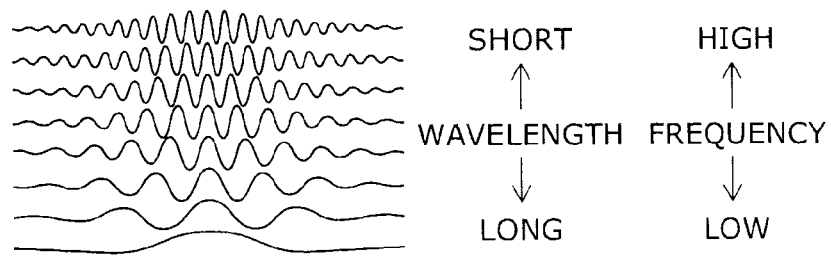
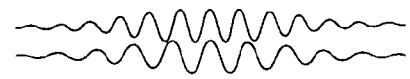
FIG. 2B
FIG. 2C
FIG. 2D
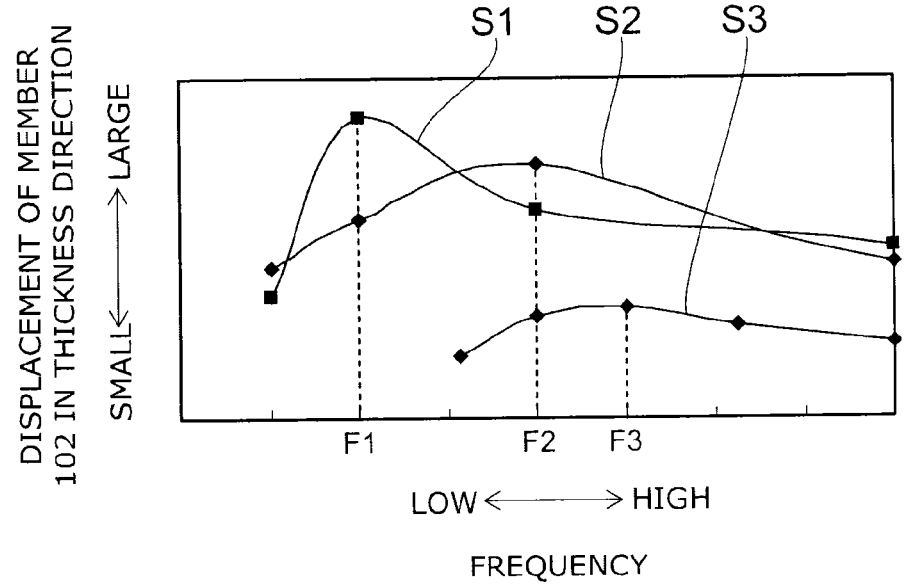
FIG. 3

ULTRASONIC INSPECTION DEVICE AND METHOD OF ULTRASONIC INSPECTION

CROSS-REFERENCE TO RELATED APPLICATIONS

This application is based upon and claims the benefit of priority from Japanese Patent Application No. 2013-061142, filed on Mar. 22, 2013; the entire contents of which are incorporated herein by reference.

FIELD

Embodiments described herein relate generally to a ultrasonic inspection device and a method of ultrasonic inspection.

BACKGROUND

There is a method of ultrasonic inspection that inspects an internal condition of an inspection target by generating ultrasonic vibration in the inspection target by irradiating laser beam on the inspection target, and analyzing the ultrasonic vibration that propagates in the inspection target.

Further, a technique is being proposed that predeterminedly calculates a frequency by which a base metal resonates, scans a position where ultrasonic vibration is to be generated and a position where the ultrasonic vibration is to be detected, calculates a dimension of a region where the base metal resonates at a lower frequency than its resonating frequency from the scanned positions, and sets the calculated dimension of the region as a dimension of a welded portion.

However, there are risks by which the method of ultrasonic inspection becomes burdensome, and an ultrasonic inspection device becomes complicated.

Due to this, a development of a technique that can easily detect the dimension of the welded portion has long been desired.

BRIEF DESCRIPTION OF THE DRAWINGS

FIGS. 2A to 2D are schematic views for illustrating how ultrasonic vibration is propagated; and FIG. 3 is a graph for illustrating an example of a frequency analysis of the ultrasonic vibration that reached a position where a laser beam is irradiated.

DETAILED DESCRIPTION

Figure 1:
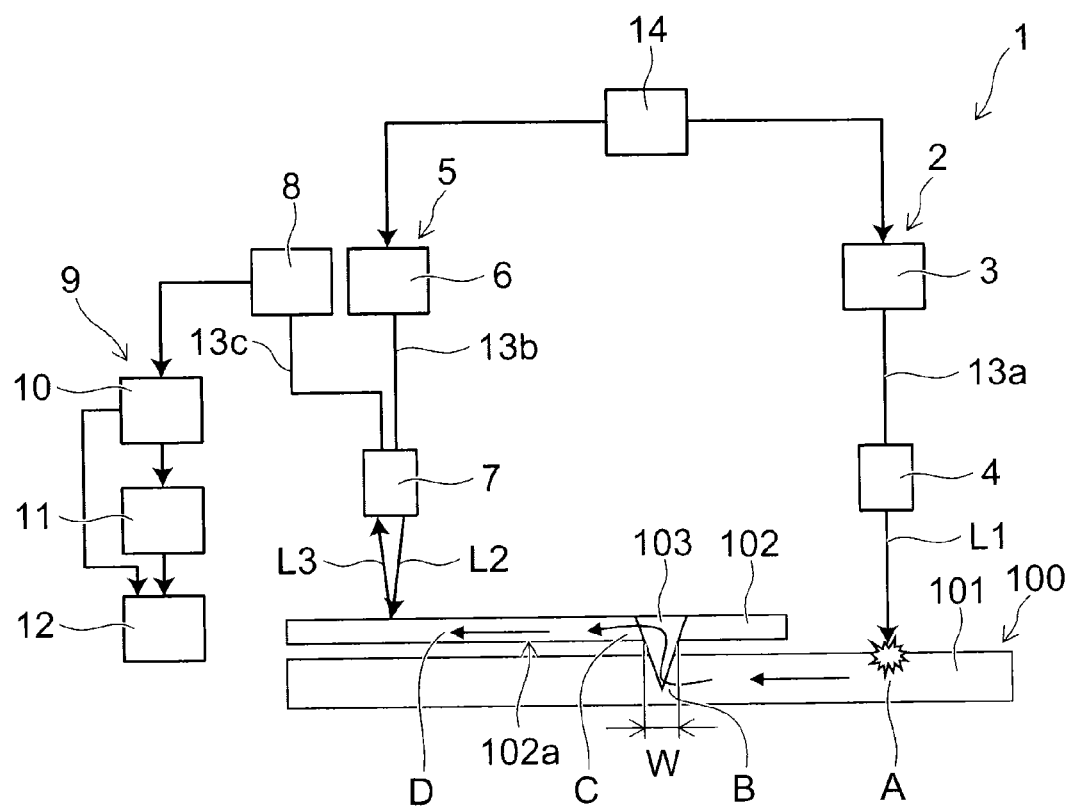
FIG. 1 is a schematic view for illustrating an ultrasonic inspection device of an embodiment.

In general, according to one embodiment, an ultrasonic inspection device includes: a vibration generating section that irradiates laser beam onto a first member to generate ultrasonic vibration; a detecting section that detects the ultrasonic vibration propagated from the first member to a second member via a welded portion; and an analyzing section that analyzes the propagated ultrasonic vibration detected by the detecting section. The analyzing section obtains at least one of frequency and wavelength of the ultrasonic vibration detected by the detecting section upon when a displacement in the second member in a thickness direction becomes maximum. The analyzing section obtains a cross sectional dimension of the welded portion from a correlated relationship of the cross sectional dimension of the welded portion obtained in advance at a position on a surface of the second member on the first member side and the at least one of the frequency and wavelength of the ultrasonic vibration.

In general, according to another embodiment, a method of ultrasonic inspection includes: generating ultrasonic vibration by irradiating laser beam onto a first member; detecting the ultrasonic vibration propagated from the first member to a second member via a welded portion; and obtaining at least one of frequency and wavelength of the ultrasonic vibration detected upon when a displacement in the second member in a thickness direction becomes maximum, and obtaining a cross sectional dimension of the welded portion from a correlated relationship of the cross sectional dimension of the welded portion obtained in advance at a position on a surface of the second member on the first member side and the at least one of the frequency and wavelength of the ultrasonic vibration.

Hereinbelow, an embodiment will be illustrated with reference to the drawings. Notably, in the respective drawings, a same reference sign is given to similar constituent elements, and a detailed description thereof will suitably be omitted.

FIG. 1 is a schematic view for illustrating an ultrasonic inspection device 1 of the embodiment.

Firstly, an inspection target 100 will be described.

As shown in FIG. 1, the inspection target 100 is welded at a portion where a member 101 (corresponding to an example of a first member) and a member 102 (corresponding to an example of a second member) are overlapped. For example, the member 101 and the member 102 are plug welded or slot welded.

The portion that had been welded is shown as a welded portion 103.

Further, a cross sectional dimension of the welded portion 103 at a position of a surface (a surface 102a illustrated in FIG. 1) of the member that is on a detecting side of ultrasonic vibration (the member 102 illustrated in FIG. 1) on a side of the member that is on a generating side of the ultrasonic vibration (the member 101 illustrated in FIG. 1) is termed W (hereinbelow simply be referred to as the cross sectional dimension W of the welded portion 103).

Notably, in FIG. 1, although a gap is provided between the member 101 and the member 102, the member 101 and the member 102 may be in contact.

No limitation is made to materials of the member 101 and the member 102. The materials of the member 101 and the member 102 may for example be metal, resin, and the like.

Here, there is a case where whether the welded portion 103 has suitable strength or not is to be inspected. In such a case, a member 102 side within the welded portion 103 where a plug or a slot is provided can be observed of its welded condition from outside.

However, a portion within the welded portion 103 formed between the member 101 and the member 102 cannot be observed of its welded condition from outside.

Further, a cross sectional dimension W of the welded portion 103 that cannot be observed from outside imposes a great influence on an aptitude of the welding strength.

Due to this, if the cross sectional dimension W of the welded portion 103 that cannot be observed from outside can be detected, the determination on the aptitude of the welding strength can be performed.

As will be described later, the ultrasonic inspection device 1 of the embodiment can easily detect the cross sectional dimension W of the welded portion 103. Further, the aptitude of the welding strength can be determined based on the detected cross sectional dimension W of the welded portion 103 and a predetermined threshold.

Next, returning to FIG. 1, the ultrasonic inspection device 1 will be illustrated.

The ultrasonic inspection device 1 is provided with a vibration generating section 2, a detecting section 5, an analyzing section 9, and a control section 14.

The vibration generating section 2 irradiates laser beam L1 to the member 101 to generate ultrasonic vibration in the member 101.

The vibration generating section 2 is provided with a laser beam source 3 (corresponding to an example of a first laser beam source) and an irradiation head 4.

The laser beam source 3 is configured capable of emitting the laser beam L1 that is of high energy and time modulated. The laser beam source 3 may for example be a pulse laser beam source. For the laser beam source 3, for example, lasers that are capable of pulse oscillation such as a YAG laser, a $CO_2$ laser, a titanium sapphire laser, and an excimer laser may be used.

However, the laser beam source 3 is not limited to the illustrated examples, and any may be adapted so long as the ultrasonic vibration can be generated in the inspection target 100.

The irradiation head 4 is connected to the laser beam source 3 via an optical fiber 13a. The irradiation head 4 irradiates the laser beam L1 emitted from the laser beam source 3 onto a surface of the member 101. The irradiation head 4 can be configured by including an optical element (for example, a lens and the like) that is not shown for concentrating the laser beam L1.

Notably, although a case in which the irradiation head 4 and the laser beam source 3 are connected via the optical fiber 13a is illustrated, no limitation is made hereto. The irradiation head 4 and the laser beam source 3 only need to be optically connected.

The detecting section 5 detects the ultrasonic vibration propagated in the member 102 welded with the member 101 at the portion where it overlaps with the member 101. That is, the detecting section 5 detects the ultrasonic vibration that is generated by the vibration generating section 2 and propagated in the member 102 from the member 101 via the welded portion 103.

Further, the detecting section 5 converts the detected ultrasonic vibration into an electric signal.

The detecting section 5 may for example be a laser interferometer.

The detecting section 5 is provided with a laser beam source 6 (corresponding to an example of a second laser beam source), a head 7, and a converting section 8.

As the laser beam source 6, a semiconductor laser may for example be used.

The head 7 is connected to the laser beam source 6 via an optical fiber 13b. Further, the head 7 is connected to the converting section 8 via an optical fiber 13c. Notably, connections are not limited to those by the optical fibers 13b, 13c, and only need to be optically connected.

The head 7 irradiates laser beam L2 emitted from the laser beam source 6 onto a surface of the member 102. Further, the head 7 receives reflected light L3 from the surface of the member 102. The head 7 can be configured by including an optical element (for example, a lens and the like) that is not shown for concentrating the laser beam L2, L3.

An optical path length of the reflected light L3 changes due to a change in a position in the surface of the member 102 (displacement of the member 102 in a thickness direction). Due to this, interfering light can be generated by causing the laser beam L2 (reference light) that was emitted from the laser beam source 6 and reflected at a reflecting surface (reference surface) in the head 7 and the reflected light L3 from the surface of the member 102 be interfered in the head 7.

An intensity of the interfering light changes depending on a distance from the reflecting surface in the head 7 to the surface of the member 102. Due to this, an amount of displacement of the member 102 in the thickness direction can be detected by the change in the intensity of the interfering light.

Further, the converting section 8 detects the ultrasonic vibration propagated in the member 102 by detecting the change in the intensity of the interfering light relative to elapsed time (displacement of the member 102 in the thickness direction relative to elapsed time).

Further, the converting section 8 converts the detected ultrasonic vibration into the electric signal. The converting section 8 can for example be configured by including a solid-state image sensing device such as CCDs (Charge Coupled Devices).

Notably, although an example in which the detecting section 5 is the laser interferometer has been illustrated, no limitation is made hereto. Any is applicable so long as the ultrasonic vibration propagated in the member 102 can be detected. For example, the detecting section 5 may be configured of a piezoelectric device.

However, an application range of the inspection target can be broadened if the detecting section 5 is configured capable of noncontact detection, such as with the laser interferometer.

The analyzing section 9 analyzes the ultrasonic vibration detected by the detecting section 5.

For example, the analyzing section 9 obtains the cross sectional dimension W of the welded portion 103 based on the ultrasonic vibration detected by the detecting section 5. Yet further, the analyzing section 9 determines the aptitude of the welding strength based on the calculated cross sectional dimension W of the welded portion 103.

The analyzing section 9 is provided with a calculating section 10, a determining section 11, and a displaying section 12.

The calculating section 10 calculates the cross sectional dimension W of the welded portion 103 based on the ultrasonic vibration detected by the detecting section 5.

The calculating section 10 calculates the cross sectional dimension W of the welded portion 103 for example by conducting a frequency analysis of the ultrasonic vibration that has reached the position where the laser beam L2 is irradiated. The frequency analysis of the ultrasonic vibration may for example be performed by a fast Fourier transformation (FFT).

For example, the calculating section 10 provided in the analyzing section 9 obtains at least one of the frequency and a wavelength of the ultrasonic vibration detected by the detecting section 5 upon when the displacement of the member 102 in the thickness direction becomes maximum. Then, the cross sectional dimension W of the welded portion 103 is obtained from a correlated relationship of a cross sectional dimension W of a welded portion as predeterminedly defined and at least one of the frequency and the wavelength of the ultrasonic vibration.

Notably, a method for obtaining the cross sectional dimension W of the welded portion 103 will be described later in detail.

The determining section 11 determines the aptitude of the welding strength based on the obtained cross sectional dimension W of the welded portion 103. For example, in a case where the obtained cross sectional dimension W of the welded portion 103 is longer than a predetermined threshold, it can be determined that the welding strength is appropriate. Contrary to this, in a case where the obtained cross sectional dimension W of the welded portion 103 is shorter than the predetermined threshold, it can be determined that the welding strength is inappropriate. Notably, the threshold can be decided by experimenting and conducting simulations on the relationship of the cross sectional dimension W of the welded portion 103 and the welding strength.

The displaying section 12 displays the cross sectional dimension W of the welded portion 103 obtained by the calculating section 10 and the determination result of the welding strength by the determining section 11. The displaying section 12 may for example be a liquid crystal display device.

The control section 14 controls the laser beam source 3 and the laser beam source 6. The control section 14 controls for example the emission of the laser beam L1 from the laser beam source 3, stoppage of the emission of the laser beam L1 and the like. The control section 14 may for example controls the emission of the laser beam L2 from the laser beam source 6, and stoppage of the emission of the laser beam L2.

Next, a method of ultrasonic inspection according to the embodiment will be illustrated together with workings of the ultrasonic inspection device 1.

Firstly, the laser beam L1 is caused to be emitted from the laser beam source 3 by the control section 14. The laser beam L1 emitted from the laser beam source 3 enters the irradiation head 4 via the optical fiber 13a. The laser beam L1 that entered the irradiation head 4 is irradiated onto the surface of the member 101. When the laser beam L1 is irradiated onto the surface of the member 101, a thermal strain and the like is generated at the surface of the member 101, and high frequency elastic waves (ultrasonic waves) are generated in the member 101. That is, the ultrasonic vibration is generated. The generated ultrasonic vibration propagates in the member 101, and propagates to the member 102 via the welded portion 103.

FIGS. 2A to 2D are schematic views for illustrating how the ultrasonic vibration is propagated.

FIG. 2A is a schematic view for illustrating the ultrasonic vibration at an A part in FIG. 1.

FIG. 2B is a schematic view for illustrating the ultrasonic vibration at a B part in FIG. 1.

FIG. 2C is a schematic view for illustrating the ultrasonic vibration at a C part in FIG. 1.

FIG. 2D is a schematic view for illustrating the ultrasonic vibration at a D part in FIG. 1.

As shown in FIG. 2A, at a position where the laser beam L1 is irradiated in the member 101 (A part in FIG. 1), the ultrasonic vibration including various wavelengths (frequencies) is generated.

Next, the ultrasonic vibration generated at the position where the laser beam L1 is irradiated in the member 101 propagates in the member 101. At this occasion, the ultrasonic vibration having a short wavelength (having a high frequency) has a property of being difficult to propagate.

Due to this, as shown in FIG. 2B, only the ultrasonic vibration having a relatively long wavelength (having a relatively low frequency) reaches the position in the vicinity of the welded portion 103 (B part in FIG. 1) in the member 101.

Further, in the occasion where the ultrasonic vibration reaches the member 102 by passing through the welded portion 103, the ultrasonic vibration having a long wavelength (having a low frequency) has a property of being difficult to propagate through the welded portion 103.

Due to this, as shown in FIG. 2C, among the ultrasonic vibration that reached the position in the vicinity of the welded portion 103 in the member 101, only the ultrasonic vibration having a short wavelength (having a high frequency) reaches the position in the vicinity of the welded portion 103 (C part in FIG. 1) in the member 102.

Here, according to the knowledge achieved by the inventors, it has been found that the wavelength (frequency) of the ultrasonic vibration that can pass through the welded portion 103 changes if the cross sectional dimension W of the welded portion 103 is changed. That is, it has been found that, as the cross sectional dimension W of the welded portion 103 becomes shorter, the wavelength (frequency) of the ultrasonic vibration that can pass through the welded portion 103 becomes shorter (higher).

The ultrasonic vibration that reached the position in the vicinity of the welded portion 103 in the member 102 propagates in the member 102. At this occasion, the ultrasonic vibration having the short wavelength (having the high frequency) has the property of being difficult to propagate.

Due to this, as shown in FIG. 2D, among the ultrasonic vibration that passed through of the welded portion 103, only the ultrasonic vibration having the long wavelength (having the low frequency) reaches the position where the laser beam L2 is irradiated (D part in FIG. 1) in the member 102.

That is, as described above, when the cross sectional dimension W of the welded portion 103 changes, the wavelength and the frequency of the ultrasonic vibration reaching the position where the laser beam L2 is irradiated changes.

Due to this, the cross sectional dimension W of the welded portion 103 can be obtained by analyzing the wavelength and frequency of the ultrasonic vibration that reached the position where the laser beam L2 is irradiated. Further, the aptitude of the welding strength can be determined based on the obtained cross sectional dimension W of the welded portion 103.

FIG. 3 is a graph for illustrating an example of a frequency analysis of the ultrasonic vibration that reached the position where the laser beam L2 is irradiated.

FIG. 3 conducted the frequency analysis on the ultrasonic vibration that reached the position where the laser beam L2 is irradiated by using a fast Fourier transform.

S1 in FIG. 3 is a case where the cross sectional dimension W of the welded portion 103 is 1 mm, S2 is a case where the cross sectional dimension W of the welded portion 103 is 0.5 mm, and S3 is a case where the cross sectional dimension W of the welded portion 103 is 0.1 mm.

As described above, the frequency of the ultrasonic vibration that can pass through the welded portion 103 becomes higher as the cross sectional dimension W of the welded portion 103 becomes shorter.

Due to this, as shown in FIG. 3, a frequency property changes according to the cross sectional dimension W of the welded portion 103. Further, it can be understood that when the cross sectional dimension W of the welded portion 103 changes, the frequency by which the displacement of the member 102 in the thickness direction becomes maximum changes. For example, in the case where the cross sectional dimension W of the welded portion 103 is 1 mm, the displacement of the member 102 in the thickness direction becomes maximum at a frequency F1. In the case where the cross sectional dimension W of the welded portion 103 is 0.5 mm, the displacement of the member 102 in the thickness direction becomes maximum at a frequency F2. In the case where the cross sectional dimension W of the welded portion 103 is 0.1 mm, the displacement of the member 102 in the thickness direction becomes maximum at a frequency F3.

That is, if a relationship of the cross sectional dimension W of the welded portion 103 and the frequency by which the displacement of the member 102 in the thickness direction becomes maximum is obtained in advance by experiments and simulations, the dimension of the cross sectional dimension W of the welded portion 103 can be obtained by detecting the frequency by which the displacement of the member 102 in the thickness direction becomes maximum. For example, if the displacement of the member 102 in the thickness direction becomes maximum at the frequency F1, it can be understood that the cross sectional dimension W of the welded portion 103 is 1 mm. For example, if the displacement of the member 102 in the thickness direction becomes maximum at the frequency F2, it can be understood that the cross sectional dimension W of the welded portion 103 is 0.5 mm. For example, if the displacement of the member 102 in the thickness direction becomes maximum at the frequency F3, it can be understood that the cross sectional dimension W of the welded portion 103 is 0.1 mm.

Further, the aptitude of the welding strength can be determined based on the cross sectional dimension W of the welded portion 103 obtained as above. For example, in a case where the obtained cross sectional dimension W of the welded portion 103 is longer than a predetermined threshold, it can be determined that the welding strength is appropriate. Contrary to this, in a case where the obtained cross sectional dimension W of the welded portion 103 is shorter than the predetermined threshold, it can be determined that the welding strength is inappropriate. The threshold can be decided by conducting experiments and simulations on the relationship of the cross sectional dimension W of the welded portion 103 and the welding strength.

Notably, by utilizing the fact that the displacement in the thickness direction becomes small when the cross sectional dimension W of the welded portion 103 becomes small, the appropriateness can be determined in a case there the displacement in the thickness direction exceeds the predetermined threshold at a peak frequency.

Notably, the above are cases of obtaining the cross sectional dimension W of the welded portion 103 based on the frequency, and determining the aptitude of the welding strength, however, for example, the cross sectional dimension W of the welded portion 103 can be obtained and the aptitude of the welding strength can be determined based on the wavelength.

As illustrated above, the method of ultrasonic inspection of the embodiment includes a process of causing the ultrasonic vibration to occur by irradiating laser beam onto the member 101, a process of detecting the ultrasonic vibration propagated to the member 102 welded to the member 101 at the portion being overlapped with the member 101, and a process of obtaining at least one of the frequency and wavelength of the ultrasonic vibration detected upon when the displacement of the member 102 in the thickness direction, and obtaining the cross sectional dimension W of the welded portion 103 from a correlated relationship of the predeterminedly obtained cross sectional dimension W of the welded portion 103 and at least one of the frequency and wavelength of the ultrasonic vibration.

In this case, the ultrasonic vibration caused to occur by irradiating the laser beam onto the member 101 and propagated to the member 102 from the member 101 via the welded portion 103 is detected in the process of detecting the ultrasonic vibration propagated in the member 102.

Further, a process of determining the aptitude of the welding strength based on the obtained cross sectional dimension W of the welded portion 103 and the predeterminedly obtained threshold may further be provided.

Further, according to the findings of the inventors, in assuming that the frequency of the ultrasonic vibration upon when the displacement of the member 102 in the thickness direction becomes maximum is F, the cross sectional dimension of the welded portion 103 is W, and a speed of the propagating ultrasonic vibration is V, it has been found that $V/5W \leq F \leq V/W$ is satisfied.

Notably, in the above, the case in which the member 101 and the member 102 are either plug welded or slot welded has been illustrated, it can be adapted to a case in which the member 101 and the member 102 are spot welded.

According to the ultrasonic inspection device 1 and the method of ultrasonic inspection of the embodiment, the cross sectional dimension W of the welded portion 103 can be obtained by irradiating the laser beam L1 onto the member 101, and analyzing the frequency and the wavelength of the ultrasonic vibration propagated in the member 102 via the welded portion 103. Further, the determination on whether the welding strength is appropriate or not can be made based on the obtained cross sectional dimension W of the welded portion 103.

That is, the cross sectional dimension W of the welded portion 103 can easily be detected. Yet further, whether the welding strength is appropriate or not can easily be determined.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:
1. An ultrasonic inspection device comprising:
  a vibration generating section that irradiates laser beam onto a first member to generate ultrasonic vibration;
  a detecting section that detects the ultrasonic vibration propagated from the first member to a second member via a welded portion, the second member and the first member being overlapped; and
  an analyzing section that analyzes the propagated ultrasonic vibration detected by the detecting section,
  the analyzing section obtaining at least one of frequency and wavelength of the ultrasonic vibration detected by the detecting section upon when a displacement of the second member in a thickness direction becomes maximum, and
  the analyzing section obtaining a cross sectional dimension of the welded portion from a correlated relationship of the cross sectional dimension of the welded portion obtained in advance at a position on a surface of the second member on the first member side and the at least one of the frequency and wavelength of the ultrasonic vibration.

2. The device according to claim 1, wherein
a following equation is satisfied:

$$V/5W \leq F \leq V/W$$

where the frequency of the ultrasonic vibration detected by the detecting section upon when the displacement of the second member in the thickness direction becomes maximum is F, the cross sectional dimension of the welded portion is W, and a speed of the propagating ultrasonic vibration is V.

3. The device according to claim 1, wherein
the vibration generating section includes a first laser beam source that emits laser beam that has high energy and is time modulated.

4. The device according to claim 3, wherein
the first laser beam source is a pulse laser beam source.

5. The device according to claim 1, wherein
the detecting section detects the ultrasonic vibration that is generated by the vibration generating section, and propagated to the second member from the first member via the welded portion.

6. The device according to claim 1, wherein
the detecting section includes:
a second laser beam source that emits laser beam;
a head that irradiates the laser beam emitted from the second laser beam source onto a surface of the second member, and causes interfering light from the laser beam and reflected light from the surface of the second member to be generated; and
a converting section that detects the ultrasonic vibration from a change in intensity of the interfering light over time.

7. The device according to claim 1, wherein
the analyzing section performs a frequency analysis of the ultrasonic vibration by fast Fourier transform.

8. The device according to claim 1, wherein
the analyzing section determines an aptitude of welding strength based on the obtained cross sectional dimension of the welded portion and a predetermined threshold.

9. The device according to claim 8, wherein
in a case where the obtained cross sectional dimension of the welded portion is longer than the threshold, the analyzing section determines that the welding strength is appropriate.

10. The device according to claim 1, wherein
the welded portion is formed by at least one type of welding selected from the group consisting of plug welding, slot welding, and spot welding.

11. A method of ultrasonic inspection comprising:
generating ultrasonic vibration by irradiating laser beam onto a first member;
detecting the ultrasonic vibration propagated from the first member to a second member via a welded portion, the second member and the first member being overlapped; and
obtaining at least one of frequency and wavelength of the ultrasonic vibration detected upon when a displacement of the second member in a thickness direction becomes maximum, and obtaining a cross sectional dimension of the welded portion from a correlated relationship of the cross sectional dimension of the welded portion obtained in advance at a position on a surface of the second member on the first member side and the at least one of the frequency and wavelength of the ultrasonic vibration.

12. The method according to claim 11, wherein
a following equation is satisfied:

$$V/5W \leq F \leq V/W$$

where the frequency of the ultrasonic vibration detected upon when the displacement of the second member in the thickness direction becomes maximum is F, the cross sectional dimension of the welded portion is W, and a speed of the propagating ultrasonic vibration is V.

13. The method according to claim 11, wherein
in the generating of the ultrasonic vibration,
the laser beam that has high energy and is time modulated is irradiated.

14. The method according to claim 13, wherein
the laser beam that has high energy and is time modulated is pulse laser.

15. The method according to claim 11, wherein
in the detecting of the ultrasonic vibration,
the ultrasonic vibration that is generated by irradiating the laser beam onto the first member, and propagated to the second member from the first member via the welded portion is detected.

16. The method according to claim 11, wherein
in the detecting of the ultrasonic vibration,
the laser beam is irradiated onto a surface of the second member, interfering light is generated from the irradiated laser beam and reflected light from the surface of the second member, and the ultrasonic vibration is detected from a change in intensity of the interfering light over time.

17. The method according to claim 11, wherein
in the obtaining of the cross sectional dimension of the welded portion,
a frequency analysis of the ultrasonic vibration is performed by fast Fourier transform.

18. The method according to claim 11, further comprising a process of:
determining an aptitude of welding strength based on the obtained cross sectional dimension of the welded portion and a predetermined threshold.

19. The method according to claim 18, wherein
in the determining of the aptitude of the welding strength,
in a case where the obtained cross sectional dimension of the welded portion is longer than the threshold, it is determined that the welding strength is appropriate.

20. The method according to claim 11, wherein
the welded portion is formed by at least one type of welding selected from the group consisting of plug welding, slot welding, and spot welding.

* * * * *